United States Patent
Mougin et al.

(10) Patent No.: US 8,449,871 B2
(45) Date of Patent: May 28, 2013

(54) COMPOSITION COMPRISING NOVEL POLYURETHANES AND COSMETIC TREATMENT PROCESS

(75) Inventors: Nathalie Mougin, Paris (FR); Xavier Schultze, Pontault-Combault (FR)

(73) Assignee: L'Oreal, Paris (FR)

( * ) Notice: Subject to any disclaimer, the term of this patent is extended or adjusted under 35 U.S.C. 154(b) by 882 days.

(21) Appl. No.: 11/723,455

(22) Filed: Mar. 20, 2007

(65) Prior Publication Data

US 2007/0283977 A1 Dec. 13, 2007

Related U.S. Application Data

(60) Provisional application No. 60/785,988, filed on Mar. 27, 2006.

(30) Foreign Application Priority Data

Mar. 20, 2006 (FR) ..................................... 06 50951

(51) Int. Cl.

| | |
|---|---|
| *A61K 8/18* | (2006.01) |
| *A61K 31/74* | (2006.01) |
| *A61K 31/785* | (2006.01) |
| *A61K 8/00* | (2006.01) |
| *A45D 7/04* | (2006.01) |
| *A61Q 1/00* | (2006.01) |
| *A61Q 5/00* | (2006.01) |
| *A61Q 5/06* | (2006.01) |
| *A61Q 19/04* | (2006.01) |
| *C08G 18/00* | (2006.01) |

(52) U.S. Cl.
USPC ........ 424/70.1; 424/59; 424/70.17; 424/70.6; 424/78.03; 424/78.35; 132/203; 132/208; 528/85

(58) Field of Classification Search
None
See application file for complete search history.

(56) References Cited

U.S. PATENT DOCUMENTS

| | | | |
|---|---|---|---|
| 3,388,087 A | 6/1968 | Dieterich et al. | |
| 4,101,473 A * | 7/1978 | Lander | ............................ 524/31 |
| 6,335,003 B1 * | 1/2002 | Kim et al. | .................. 424/70.17 |
| 6,939,938 B2 | 9/2005 | Benard et al. | |
| 2003/0235548 A1 * | 12/2003 | Lu | ............................. 424/70.12 |
| 2004/0052753 A1 | 3/2004 | Mougin | |
| 2004/0202622 A1 * | 10/2004 | Quadir | ........................... 424/59 |
| 2005/0169873 A1 | 8/2005 | Rollat et al. | |
| 2006/0067907 A1 | 3/2006 | Mougin et al. | |

FOREIGN PATENT DOCUMENTS

| | | |
|---|---|---|
| EP | 0 619 111 B1 | 10/1994 |
| EP | 1 329 470 A1 | 7/2003 |
| EP | 1 543 819 A1 | 6/2005 |
| EP | 1 645 579 A1 | 4/2006 |
| WO | WO 94/13724 | 6/1994 |
| WO | WO 02/09655 A2 | 2/2002 |
| WO | WO 02/32978 A1 | 4/2002 |
| WO | WO 02/36653 A2 | 5/2002 |

OTHER PUBLICATIONS

French Search Report for FR 0650951 (French priority application for the present application), dated Oct. 19, 2006.

* cited by examiner

*Primary Examiner* — Robert A Wax
*Assistant Examiner* — Danah Al-Awadi
(74) *Attorney, Agent, or Firm* — O'Brien Jones, PLLC

(57) ABSTRACT

The present disclosure relates to novel polyurethanes comprising cationic units, of diisocyanates and of nonionic units derived from polyolefins comprising at least 10 mol % of units comprising at least one residual carbon-carbon double bond.

The present disclosure also relates to cosmetic or pharmaceutical compositions comprising the polyurethanes, and also to a cosmetic treatment process, for example for shaping and/or holding the hair, comprising the application of such a composition.

43 Claims, No Drawings

COMPOSITION COMPRISING NOVEL POLYURETHANES AND COSMETIC TREATMENT PROCESS

This application claims benefit of U.S. Provisional Application No. 60/785,988, filed Mar. 27, 2006, the contents of which are incorporated herein by reference. This application also claims benefit of priority under 35 U.S.C. §119 to French Patent Application No. FR 06 50951, filed Mar. 20, 2006, the contents of which are also incorporated herein by reference.

The present disclosure relates to novel polymers, such as cationic polyurethanes of elastic nature, and also to their use in cosmetic or pharmaceutical compositions, and to the cosmetic or pharmaceutical compositions thus obtained.

The formation of deposits and films with elastic properties has always been a subject of considerable research in cosmetics. The reason for this is that most of the areas of the human body liable to receive cosmetic deposits, such as the skin, the lips, the hair, the eyelashes and the nails, are subject to large mechanical stresses and deformations. Cosmetic films and deposits must be able to withstand these stresses and to follow these deformations without breaking.

The use of polyurethanes in cosmetics has been known for a long time and is described, for example, in International Patent Application No. WO 94/13724 and European Patent No. 619 111.

However, the polyurethanes described in these documents have glass transition temperatures (Tg) greater than room temperature (20° C.), which means that at room temperature, they may be in vitreous form and form brittle films, which are unacceptable for cosmetic use.

Physiologically acceptable polymers with low glass transition temperatures exist, for instance acrylic polymers, but these polymers form very tacky deposits, which is a drawback in the majority of cosmetic applications.

Physiologically acceptable polyurethanes that form non-tacky, non-brittle films capable of plastic and elastic deformations are known, for example, from International Patent Application No. WO 02/32978. These advantageous viscoelastic properties are due to the presence in the polymer of long macromolecular units of relatively low glass transition temperature, which, at room temperature, are not in vitreous form.

The polymers described may, for instance, comprise macromolecular units of polyether type, such as polytetramethylene oxide (PTMO), or alternatively of (ethylene-butylene) copolymer type.

Additionally, U.S. Pat. No. 3,388,087 describes polyurethanes comprising polypropylene glycol ether or polybutylene glycol ether units. These polymers comprise hygroscopic units, which is detrimental to the cosmetic quality of the polymer applied to the hair; the polymer may then be too hydrophilic, tacky and/or sparingly water-resistant.

Accordingly, one aspect of the present disclosure is to obtain physiologically acceptable polymers, such as polyurethanes, with improved film-forming and viscoelastic properties.

Polymers, such as of the polyurethane type, that make it possible to obtain a cosmetic composition with better humidity and/or water resistance, and thus sufficient resistance over time of the styling nature, are also sought.

The present disclosure also relates to the use of specific polymers, obtained from polyolefins, and which have a hydrophobic nature, such that the styling products, for instance hair gels, sprays and/or foams, comprising them make it possible to give the hair hold while at the same time conserving sufficient resistance over time of this styling.

This is beneficial, for example, during the production of styling with "strands" (tufts).

The present disclosure thus relates to a polyurethane comprising:
(a1) at least one cationic or cationizable unit derived from at least one tertiary or quaternary amine comprising at least two reactive functions containing labile hydrogen,
(a2) at least one nonionic unit derived from at least one polyolefin comprising at least two reactive functions containing labile hydrogen, the polyolefin comprising at least 10 mol % of units comprising at least one C=C (carbon-carbon) double bond, relative to the total amount of units forming the polyolefin;
(b) at least one unit derived from a compound comprising at least two isocyanate functions.

The present disclosure also relates to a composition comprising at least one such polyurethane in a physiologically acceptable medium. This polymer may be of elastic nature, i.e., may be a macromolecular material that rapidly returns to its initial form and dimensions after a low stress that has produced a large deformation has ceased.

By virtue of its cationic/cationizable nature, the polymer disclosed herein may have the benefit of having excellent affinity for keratin substrates such as the hair, the nails and the horny layer of the epidermis, to which keratin gives a negative charge.

The use of the presently disclosed polymer in lakes and styling compositions also may make it possible to improve the flexibility of the styling, i.e., to obtain more natural and more durable resistance of the hair than that obtained with the fixing polymers of the prior art.

Finally, in at least one embodiment, the polymers are not tacky, which facilities their use in cosmetics. And also in at least one embodiment, the compositions comprising a polymer according to the present disclosure have better water resistance by virtue of the use of olefin copolymers of hydrophobic nature.

The presently disclosed polymer may be obtained by polycondensation of compounds bearing reactive functions comprising labile hydrogen with compounds comprising at least two isocyanate functions.

As used herein, the term "reactive functions containing labile hydrogen" is understood to mean functions capable, after loss of a hydrogen atom, of forming covalent bonds with the isocyanate functions of compounds comprising at least two isocyanate functions. Non-limiting examples of such functions that may be mentioned include hydroxyl, primary amine or secondary amine groups, or thiol groups.

Depending on the nature of the reactive functions bearing the labile hydrogen (—OH, —$NH_2$, —NHR or —SH), the polycondensation leads, respectively, to polyurethanes, polyureas or polythiourethanes. Thus, the polymers disclosed herein may be urethane/urea and/or thiourethane copolymers. All these polymers are combined in the present disclosure, for the sake of simplicity, under the term "polyurethanes".

The cationic or cationizable polyurethane disclosed herein thus comprises at least one cationic or cationizable unit (a1) resulting from at least one tertiary or quaternary amine comprising at least two reactive functions containing labile hydrogen.

As used herein, the term "cationic or cationizable unit" is understood to mean any unit which, either by its intrinsic chemical nature, or as a function of the medium and/or the pH in which it is present, will be in cationic form.

In at least one embodiment of the present disclosure, the tertiary amine is protonatable at a pH chosen from pH 1 to pH 12. As used herein, the term "protonatable" is understood to mean that the tertiary amine function may be at least partially neutralized with a neutralizer or as a function of the medium in which it is formulated.

When the tertiary or quaternary amines forming the units (a1) bear more than two functions containing labile hydrogen, the polyurethane obtained has a branched structure. However, in one embodiment of the present disclosure, the tertiary or quaternary amines forming the units (a1) comprise only two reactive functions containing labile hydrogen and the polyurethanes obtained via polycondensation consequently have an essentially linear structure.

It is also possible to use a mixture of difunctional amines comprising a small proportion of amines bearing more than two reactive functions comprising labile hydrogen.

The tertiary or quaternary amines forming the cationic or cationizable units (a1) are, in one embodiment, chosen from compounds corresponding to one of the following formulae:

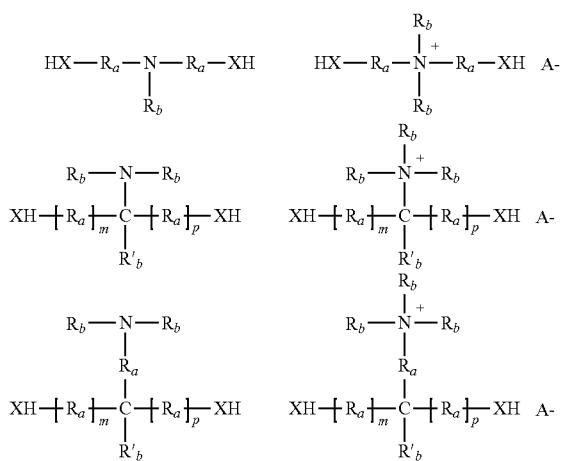

wherein:
- each $R_a$, independently of each other, is chosen from linear or branched divalent $C_1$-$C_6$ alkylene groups, or alternatively from $C_3$-$C_6$ cycloalkylene and arylene groups and mixtures thereof; these groups optionally being substituted with at least one halogen atom and/or comprising at least one heteroatom chosen from O, N, P and S,
- each $R_b$ is chosen from, independently of each other, linear or branched $C_1$-$C_6$ alkyl groups, or alternatively from $C_3$-$C_6$ cycloalkyl and aryl groups, and mixtures thereof; these groups optionally being substituted with at least one halogen atom and/or comprising at least one heteroatom chosen from O, N, P and S,
- each $R'_b$ is chosen from H and linear or branched $C_1$-$C_6$ alkyl groups, or alternatively from $C_3$-$C_6$ cycloalkyl and aryl groups, and mixtures thereof; these groups optionally being substituted with at least one halogen atom and/or comprising at least one heteroatom chosen from O, N, P and S,
- m and p are, independently of each other, equal to 0 or 1; in one embodiment m=1 and p=1;
- each X is chosen from, independently of each other, oxygen and sulfur atoms, and groups NH or $NR_c$, wherein $R_c$ is chosen from a $C_1$-$C_6$ alkyl group, and
- $A^-$ is chosen from a physiologically acceptable counterion, for example a halide such as chloride or bromide.

In one embodiment of the present disclosure, the amines are of formula:

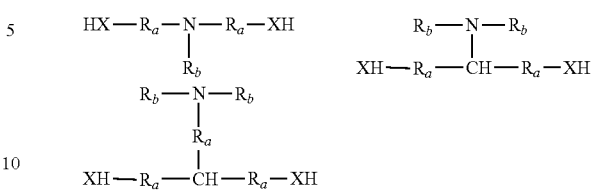

wherein Ra is a linear or branched divalent $C_1$-$C_6$ alkylene group, such as methylene or ethylene, Rb is a linear or branched $C_1$-$C_6$ alkyl group, such as a methyl, ethyl, n-butyl, isobutyl or tert-butyl group, and X is equal to O.

In yet another embodiment of the present disclosure, the amines are of formula:

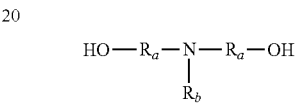

wherein Ra is a linear or branched divalent $C_1$-$C_6$ alkylene group, such as methylene or ethylene; and Rb is a linear or branched $C_1$-$C_6$ alkyl group, such as a methyl, ethyl, n-butyl, isobutyl or tert-butyl group.

As tertiary amines that may be used in at least one embodiment herein, mention may be made of N-methyldiethanolamine and N-tert-butyldiethanolamine.

The protonatable tertiary amines may be totally or partially neutralized with a neutralizer of organic acid type comprising at least one carboxylic, sulfonic and/or phosphonic acid function or with a mineral acid. Non-limiting examples of acids include hydrochloric acid, sulfuric acid, acetic acid, propionic acid, citric acid, gluconic acid, tartaric acid, lactic acid, phosphoric acid, benzoic acid, stearic acid, oleic acid, 2-ethylcaproic acid, behenic acid and betaine hydrochloride, and a mixture thereof.

The cationic polyurethane according to the present disclosure also comprises at least one nonionic unit (a2) resulting from at least one polyolefin comprising at least two reactive functions containing labile hydrogen, the polyolefin comprising at least 10 mol % of units comprising at least one C=C double bond (residual), relative to the total amount of units forming the polyolefin.

In at least one embodiment, the at least one polyolefin may be nonionic.

In at least one embodiment, the reactive functions containing labile hydrogen are located at the ends of the polyolefin. The reactive functions containing labile hydrogen may be, for example, hydroxides. In at least one embodiment, the number of hydroxide units is close to or even equal to 2.

In at least one embodiment of the present disclosure, the at least one polyolefin forming the unit (a2) is chosen from olefin homopolymers and/or copolymers, bearing at their ends reactive functions containing labile hydrogen and having a glass transition temperature (Tg), measured by differential thermal analysis (DSC, differential scanning calorimetry) according to ASTM standard D3418-97, of less than 10° C.

The polyurethane according to the present disclosure may comprise several units (a2) resulting from several identical or different polyolefins (polyolefin mixtures); however, in this case, each of the polyolefins comprises at least 10 mol % of units comprising at least one C=C double bond.

As used herein, the term "unit comprising a C=C double bond" is understood to mean a unit comprising at least one residual C=C double bond, for example only one double bond; it may be, for example, a unit derived from the polymerization of a butadiene or isoprene unit, all isomeric forms included (cis or trans, 1,2- or 1,4-).

The polyolefin according to the present disclosure may be, for instance, an olefin homopolymer. Non-limiting examples that may be mentioned include 1,2-butadiene, 1,4-butadiene or isoprene homopolymers, and:

1,4-polybutadienes, in their cis and trans forms:

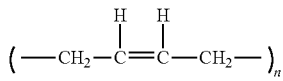

1,2-polybutadienes: —[CH2-CH(CH=CH2)-]n
poly(cis-1,4-isoprenes):

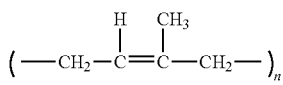

poly(trans-1,4-isoprenes):

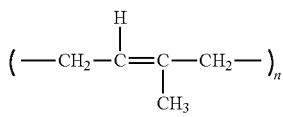

The polyolefin according to the present disclosure may also be a copolymer of different olefins (olefin copolymer), provided that the final polyolefin comprises at least 10 mol % of units comprising at least one C=C double bond.

In one embodiment of the present disclosure, the polyolefin may consist exclusively of units comprising at least one C=C double bond. Non-limiting examples that may be mentioned include copolymers, such as statistical copolymers, comprising 1,2-butadiene units and/or 1,4-butadiene units in its cis and/or trans forms, and/or isoprene units, such as cis-1,4-isoprene and trans-1,4-isoprene, as a mixture. Non-limiting mention may be made of (1,2-butadiene/1,4-butadiene) statistical copolymers.

In at least one embodiment of the present disclosure, the polyolefins may be statistical and with hydroxyl end groups and correspond to the following structure:

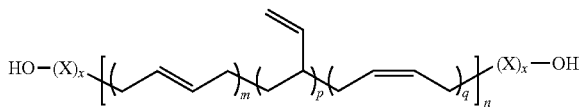

in which:
m, p and q are mole fractions from 0 to 1, and m+p+q is equal to 1; in at least one embodiment, m may range from 0.1 to 0.8, or further, from 0.15 to 0.7; p may range from 0.1 to 0.8, or further from 0.15 to 0.7; and q may range from 0.05 to 0.5, or further from 0.1 to 0.4;
n is an integer ranging from 10 to 100, such as from 15 to 50;
x is 0 or 1, and
X is a divalent carbon-based radical, such as linear, cyclic or branched alkylene, comprising 1 to 10 carbon atoms; for instance methylene, ethylene, propylene or isopropylene.

The divalent carbon-based radicals may, for instance, have a number-average molecular mass, Mn, ranging from 400 to 50 000, further for example from 500 to 30 000, even further for example from 1000 to 15 000, such as from 1500 to 12 000.

Non-limiting mention may be made of:
polybutadienes with hydroxyl end groups, such as the polymers of structure:

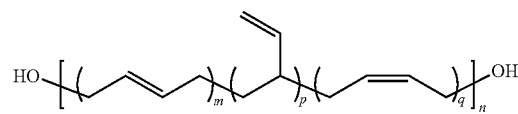

with m=0.6, p=0.2 and q=0.2 (mole fractions) and n=25.
Non-limiting mention may be made of the commercial products Poly bd R20LM and Poly bd R45HTLO from Sartomer;
polybutadienes with primary hydroxyl end groups, such as the polymers that may be represented by the following structure:

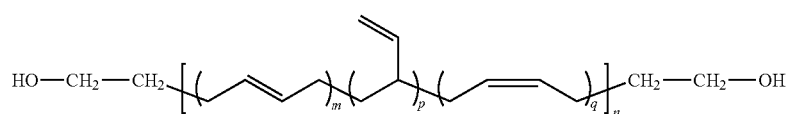

which are statistical copolymers of 1,4-cis-butadiene and of 1,4-trans-butadiene, with m=0.17, p=0.65 and q=0.18 (mole fractions) and n is such that the number-average molecular weight Mn ranges from 1000 to 10 000 and for instance from 2000 to 6000 (g·mol$^{-1}$).

Non-limiting mention may be made of the commercial products Krasol LBH-P 2000, 3000 or 5000 from Sartomer;
polybutadienes with secondary hydroxyl end groups, such as the polymers that may be represented by the following structure:

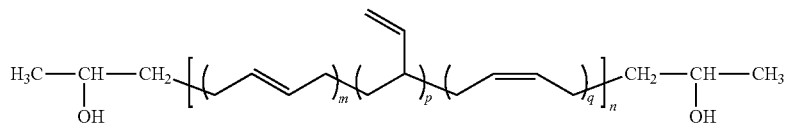

which are statistical copolymers of 1,4-cis-butadiene and of 1,4-trans-butadiene, with m=0.17, p=0.65 and q=0.18 (mole fractions), and n is such that the number-average molecular weight Mn ranges from 1000 to 12 000 and for example from 2000 to 10 000 (g.mol$^{-1}$).

Non-limiting mention may be made of the commercial products Krasol LBH 2000, 3000, 5000 or 10 000 from Sartomer.

In another embodiment, the polyolefin may also comprise additional units not comprising a C═C double bond.

However, these additional units are present in a maximum amount of 90 mol %, given that the final polyolefin should comprise at least 10 mol % of units comprising at least one C═C double bond.

These additional olefin units may be chosen, in at least one embodiment, from ethylene —(CH$_2$—CH$_2$)$_n$—, propylene —(CH$_2$—CH$_2$—CH$_2$)$_n$— or isopropylene —(CH$_2$CH(CH$_3$))$_n$— units, and/or butylene units of formula:

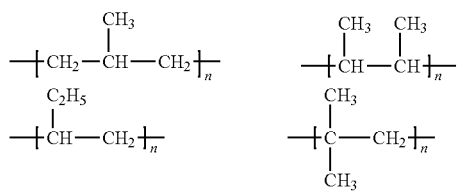

and also mixtures thereof.

The olefin homopolymers or copolymers as defined above may undergo, after polymerization, a partial hydrogenation of the residual double bonds. This hydrogenation cannot in any way be total.

Specifically, the polyolefins that may be used to form the units (a2) according to the present disclosure comprise, in at least one embodiment, at least 10 mol % of units comprising at least one C═C double bond (residual), relative to the total amount of units forming the polyolefin. They polyofeins may comprise at least 20 mol %, for instance at least 40 mol %, or further, at least 50 mol %, or even further, at least 80 mol %, or finally 100 mol %, of units comprising at least one C═C double bond, for example comprising only one C═C double bond.

This content of units comprising at least one C═C double bond maybe determined via the usual techniques, for example via NMR or iodine assay.

In at least one embodiment of the present disclosure, the polyolefin(s) forming the nonionic units (a2) have a number-average molecular mass (Mn) ranging from 400 to 50 000, for instance from 500 to 30 000, further, for instance, from 1000 to 15 000 and even further from 1500 to 12 000.

Non-limiting examples of the polyolefins that may be used in the context of the present disclosure are:
homopolymers such as 1,4-polybutadiene and 1,2-polybutadiene;
copolymers of structure:

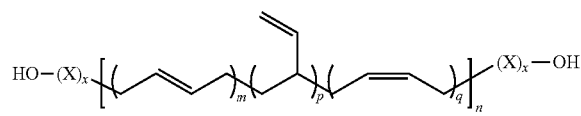

with
m, p and q being mole fractions ranging from 0 to 1, and m+p+q=1; for example m being from 0.1 to 0.8, or from 0.15 to 0.7; p being from 0.1 to 0.8, or from 0.15 to 0.7; and q being from 0.05 to 0.5, or from 0.1 to 0.4;
n is an integer ranging from 10 to 100, for instance from 15 to 50;
x is 0 or 1, and
X is a divalent carbon-based radical, for example linear, cyclic or branched alkylene comprising 1 to 10 carbon atoms; for instance methylene, ethylene, propylene or isopropylene.

The cationic polyurethane according to the present disclosure also comprises at least one unit (b) resulting from at least one compound comprising at least two isocyanate functions. It may further be a mixture of several compounds comprising at least two isocyanate functions.

The compounds comprising at least two isocyanate functions may be chosen from diisocyanates, or mixtures of a diisocyanate and a polyisocyanate comprising more than two isocyanate functions, the polyisocyanate, for example, representing from 0.1% to 40% of the weight of the mixture, such as from 0.5% to 35% by weight or even from 1% to 30% by weight relative to the weight of the mixture.

The compounds comprising at least two isocyanate functions may, for instance, be chosen from conjugated or non-conjugated, aromatic or non-aromatic cyclic aliphatic diisocyanates. They may be chosen, for example, from methylenediphenyl diisocyanate, methylenecyclohexane diisocyanate, isophorone diisocyanate, toluene diisocyanate, naphthalene diisocyanate, 1,4-butane diisocyanate and 1,6-hexane diisocyanate, and mixtures thereof; such as isophorone diisocyanate.

In one embodiment, the polyurethane according to the present disclosure comprises:
at least one cationic unit resulting from amines of formula:

-continued

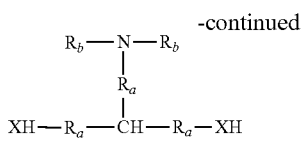

in which:

$R_a$ is a linear or branched divalent $C_1$-$C_6$ alkylene group, for example methylene or ethylene;

$R_b$ is a linear or branched $C_1$-$C_6$ alkyl group, for example a methyl, ethyl, n-butyl, isobutyl or tert-butyl group;

and X is equal to O;

at least one nonionic unit resulting from polyolefins chosen from 1,4-polybutadiene and 1,2-polybutadiene homopolymers; or copolymers of structure:

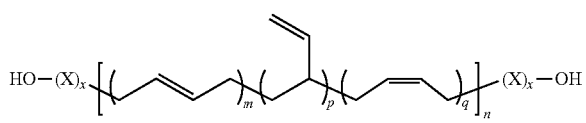

with m, p and q being mole fractions ranging from 0 to 1, and m+p+q=1; for example m ranges from 0.1 to 0.8, or from 0.15 to 0.7; p ranges from 0.1 to 0.8, or from 0.15 to 0.7; and q ranges from 0.05 to 0.5, or from 0.1 to 0.4;

n is an integer ranging from 10 to 100, for instance from 15 to 50;

x is 0 or 1, and

X is a divalent carbon-based radical, such as linear, cyclic or branched alkylene, comprising 1 to 10 carbon atoms; such as methylene, ethylene, propylene or isopropylene; and at least one unit resulting from aliphatic diisocyanates.

In another embodiment of the present disclosure, the polyurethanes disclosed herein comprise:

at least one cationic unit resulting from amines of formula:

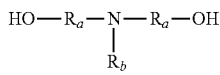

wherein $R_a$ is a linear or branched divalent $C_1$-$C_6$ alkylene group, such as methylene or ethylene; and $R_b$ is a linear or branched $C_1$-$C_6$ alkyl group, such as a methyl, ethyl, n-butyl, isobutyl or tert-butyl group; for example, N-methyldiethanolamine and N-tert-butyldiethanolamine;

at least one nonionic unit resulting from polyolefins of structure:

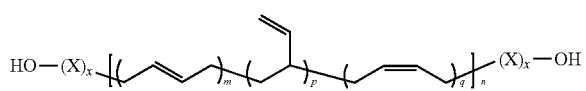

with m, p and q being mole fractions from 0 to 1, and m+p+q=1; for example m ranges from 0.1 to 0.8, or from 0.15 to 0.7; p ranges from 0.1 to 0.8, or from 0.15 to 0.7; and q ranges from 0.05 to 0.5, or from 0.1 to 0.4;

n is an integer ranging from 10 to 100 and for example from 15 to 50;

x is 0 or 1, and

X is a divalent carbon-based radical, such as linear, cyclic or branched alkylene, comprising 1 to 10 carbon atoms; such as methylene, ethylene, propylene or isopropylene; and at least one unit resulting from diisocyanates chosen from methylenecyclohexane diisocyanate, isophorone diisocyanate, 1,4-butane diisocyanate and 1,6-hexane diisocyanate, and a mixture thereof; such as isophorone diisocyanate.

The polyurethane according to the present disclosure comprises units (a1), (a2) and (b) as defined above, and in at least one embodiment does not comprise additional units other than these.

The physical parameter that best characterizes the viscoelastic properties of the cationic polyurethane according to the present disclosure is its instantaneous strain recovery Ri. The cationic polyurethane of the present disclosure has, for instance, an instantaneous recovery ($R_i$), measured under the conditions indicated below, before the examples section, ranging from 5% to 95%, for example from 20% to 90%, further for example from 50% to 85%, even further for example from 55% to 85%.

The viscosity of the polyurethane according to the present disclosure, measured at 10% in tetrahydrofuran (THF), at 25° C., with a Brookfield viscometer, needle module, ranges from 1 to 1000 cps, for instance from 1 to 100 cps and further, for instance, from 2 to 80 cps. The polyurethane is characterized in non-neutralized form.

In another embodiment of the present disclosure, the polyurethane has at least two glass transition temperatures (Tg), at least one of which is less than 10° C., for example less than 0° C. and even further, for example, less than −10° C., and at least one other is greater than or equal to room temperature (20° C.).

The instantaneous recovery and consequently the viscoelastic properties of the polyurethane according to the present disclosure depend on the nature and the amount of the various units (a1), (a2) and (b).

The fraction of cationic units (a1), in at least one embodiment, is sufficient to give the polymers their positive charge responsible for their good affinity for keratin substrates.

The nonionic unit(s) (a2), in at least one embodiment, represent a weight fraction sufficient for the polyurethanes to have at least one glass transition temperature of less than 10° C. and not to form brittle films.

The amines forming the cationic or cationizable units (a1) represent from 0.1% to 50%, for example from 1% to 30% and further for example from 5% to 20% by weight, relative to the total weight of the final polyurethane.

The polyolefins forming the nonionic units (a2) represent from 30% to 99% by weight, for example from 50% to 90% and further, for example, from 60% to 80% by weight, relative to the total weight of the final polyurethane.

The compounds comprising at least two isocyanate functions, forming the units (b), are present in an essentially stoichiometric amount relative to the sum of the tertiary/quaternary amines forming the units (a1) and of the polyolefins forming the units (a2).

The production of polyurethanes with high molar masses assumes a number of isocyanate functions that is virtually identical to the number of functions containing labile hydrogen. A person skilled in the art will know how to select a possible molar excess of one or the other type of function to adjust the molar mass to the desired value.

Thus, the compounds comprising at least two isocyanate functions forming the units (b) represent from 1% to 60% by weight, for example from 5% to 50% by weight and further for example from 15% to 35% by weight, relative to the total weight of the final polyurethane.

In order to form the polyurethane according to the present disclosure, the following may be used:
- 20 mol % to 55 mol %, for example from 25 mol % to 50 mol % or further for example from 30 mol % to 47 mol % of tertiary and/or quaternary amine(s) capable of forming the units (a1);
- 1 mol % to 30 mol %, for example from 2 mol % to 25 mol % or further for example from 3 mol % to 20 mol % of polyolefin(s) capable of forming the units (a2); and
- 30 mol % to 65 mol %, for example from 35 mol % to 60 mol % or further for example from 45 mol % to 55 mol % of compound(s) comprising at least two isocyanate functions capable of forming the units (b).

The mole ratio between (b) and (a1)+(a2) may, for example, be 1, such as from 0.9 to 1.1.

The cationic or cationizable polyurethane of elastic nature according to the present disclosure finds an application, for example, in cosmetics and pharmaceuticals. Thus, it may be incorporated into many cosmetic compositions, in which it will improve the cosmetic properties, for example in terms of styling.

The amount of polyurethane present in the compositions depends on the type of composition and on the desired properties, and may vary within a wide range, ranging from 0.1% to 90% by weight, for example from 1% to 50% by weight, for example from 2% to 25% by weight, or even, for example, from 5% to 15% by weight, and even further, for example, from 6% to 10% by weight, relative to the weight of the final cosmetic or pharmaceutical composition.

Thus, when the polyurethane according to the present disclosure is intended to be incorporated into hair compositions such as hair lacquers, its content may, for example, range from 0.1% to 25% by weight, further, for example, from 1% to 20% by weight, even further, for example, from 2% to 15% by weight, or from 4% to 8% by weight, relative to the weight of the final composition.

When it is intended to be incorporated into styling compositions, it may represent from 0.5% to 20% to weight, for example, from 1% to 15% by weight, further, for example, from 2% to 10% by weight, or even further, for example, from 5% to 8% by weight, relative to the weight of the composition.

When it is intended to be incorporated into compositions of shampoo type, it may represent from 0.1% to 20% by weight, for example from 0.5% to 15% by weight, further for example from 1% to 10% by weight or even further, for example, from 2% to 5% by weight, relative to the weight of the composition.

The compositions according to the present disclosure may be in any galenical form conventionally used for topical application, such as in the form of an aqueous, alcoholic or aqueous-alcoholic solution or suspension, an oily solution or suspension, a solution or dispersion of the lotion or serum type, an emulsion of liquid or semi-liquid consistency of the milk type, obtained by dispersing a fatty phase in an aqueous phase (O/W) or conversely (W/O), a suspension or emulsion of soft consistency of the (O/W) or (W/O) cream type, an aqueous or anhydrous gel, an ointment, a loose or compacted powder to be used in its native form or to be incorporated into an excipient, or any other cosmetic form.

The cosmetic or pharmaceutical compositions according to the present disclosure comprise, besides the polymers, a physiologically acceptable, e.g., a cosmetically or pharmaceutically acceptable, medium, such as a dermatologically acceptable medium, i.e., a medium that is compatible with cutaneous tissue, for instance facial or bodily skin, and keratin materials such as the hair, the eyelashes, the eyebrows and the nails.

The physiologically acceptable medium comprises a solvent medium or a dispersion of polymers according to the present disclosure, which may comprise at least one compound chosen from water, alcohols, polyols, esters, carbon-based oils, silicone oils and fluorosilicone oils, and mixtures thereof.

The physiologically acceptable medium of the compositions, as disclosed herein, may comprise water or a mixture of water and of hydrophilic organic solvent(s), for instance alcohols such as linear or branched $C_1$-$C_6$ monoalcohols, for instance ethanol, tert-butanol, n-butanol, isopropanol, n-propanol or 2-butoxyethanol; and polyols, for instance glycerol, diglycerol, ethylene glycol, propylene glycol, sorbitol, pentylene glycol and polyethylene glycols, or alternatively polyol or glycol ethers, e.g., of $C_2$ such as diethylene glycol monoethyl ether and monomethyl ether, and hydrophilic $C_2$-$C_4$ aldehydes.

The composition according to the present disclosure may also comprise at least one cosmetically acceptable adjuvant used in cosmetic compositions intended to be applied to keratin fibers.

Non-limiting mention of cosmetically acceptable adjuvants useful herein includes: gelling agents and/or thickeners; associative or non-associative polymers; anionic, nonionic, cationic and/or amphoteric surfactants; pro-penetrating agents, emulsifiers, fragrances, preserving agents, fillers, sunscreens; dyestuffs, proteins, vitamins, provitamins; fixing or non-fixing, anionic, nonionic, cationic or amphoteric polymers; moisturizers, emollients, softeners; mineral, plant or synthetic oils; hydrophilic or lipophilic active agents, for instance ceramides and pseudoceramides; antifoams, antiperspirants, free-radical scavengers, bactericidal agents and antidandruff agents.

A person skilled in the art will take care to select the optional additives and the amount thereof such that they do not harm the properties of the compositions of the present disclosure.

The composition according to the present disclosure may be in the form of a thickened or non-thickened lotion, a thickened or non-thickened cream, a gel, a mousse or any other suitable form. It may optionally be packaged in a pump-dispenser bottle or in an aerosol container.

The cosmetic composition according to the present disclosure may be in the form of a care, cleansing and/or makeup product for bodily or facial skin, the lips, the eyelashes, the nails and the hair, an antisun product or self-tanning product, a body hygiene product or a hair product, such as a product for caring for, cleansing, styling or coloring the hair.

The composition according to the present disclosure may be applied in the field of hair care, such as for holding the hairstyle or for shaping the hair, or alternatively for cleansing the hair. The hair compositions may be, for example, shampoos, hair conditioners, styling or care gels, care lotions or creams, conditioners, hair setting lotions, blow-drying lotions, and fixing and styling compositions such as lacquers or sprays. The lotions may be packaged in various forms, such as in vaporizers or pump-dispenser bottles or in aerosol containers in order to allow application of the composition in vaporized form or in the form of a mousse.

It may also be in the form of a hair coloring product; or in the form of a permanent-waving, relaxing or bleaching composition or alternatively in the form of rinse-out compositions, to be applied before or after dyeing, bleaching, permanent-waving or relaxing the hair or alternatively between the two steps of a permanent-waving or hair-relaxing operation.

The composition according to the present disclosure may also be in the form of a care composition, such as a moisturizing composition, for the skin, the lips and/or the integuments, or in the form of a skin cleansing composition, for example a makeup-removing product or a bath or shower gel.

It may also be in the form of an uncolored care product, intended for treating the skin and especially for moisturizing it, making it smooth, depigmenting it, nourishing it, protecting it against solar rays, or giving it a specific treatment.

It may also be in the form of a body hygiene composition, such as in the form of a deodorant or antiperspirant product, or alternatively in the form of a hair-removing composition.

It may also be in the form of a makeup product, such as a colored makeup product, for bodily or facial skin, or for the hair, for example a foundation, optionally having care properties, a blusher, a makeup rouge, an eyeshadow, a concealer product, an eyeliner, a lip makeup product, for instance a lipstick, optionally having care properties, a lip gloss, lip pencils; a makeup product for the integuments, for instance the nails or the eyelashes, for example in the form of a mascara cake, or for the eyebrows and the hair; a temporary tattoo product for bodily skin.

The composition according to the present disclosure may also be a hair composition for styling the hair, and may be in the form of a gel, a mousse or a spray.

Still another aspect of the present disclosure is a cosmetic treatment process, such as for making up, caring for, cleansing, coloring or shaping keratin materials, for example bodily or facial skin, the nails, head hair, bodily hair and/or the eyelashes, comprising the application to the materials of a cosmetic composition as defined above.

In at least one embodiment, the present disclosure relates to a cosmetic treatment process for shaping and/or holding the hair, comprising the application of a composition according to the present disclosure to the hair; optionally followed by a rinsing step.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The following examples are intended to illustrate the present disclosure in a non-limiting manner.

EXAMPLES

Determination of the Molar Masses

The weight-average (Mw) and number-average (Mn) molar masses were determined by gel permeation liquid chromatography or GPC (THF solvent, calibration curve established with linear polystyrene standards, refractomeric detector).

The dispersity index was calculated in the following manner: Ip=Mw/Mn

The GPC was performed with Styragel HR4/7.8×300 mm columns, sold by Waters WAT044225.

The detection was performed with a Waters 410 refractometer.

The eluent was THF (tetrahydrofuran) at a flow rate of 1 ml/minute.

The volume injected was 50 microliters, at 25° C.

The calibration was performed using polystyrene standards.

Determination of the Instantaneous Recovery Ri

The physical parameter that best characterizes the viscoelastic properties of the polyurethane according to the present disclosure is its instantaneous strain recovery.

This recovery was determined by means of a creep test under tension, which consists in rapidly stretching a sample to a predetermined degree of elongation, followed by releasing the stress and measuring the length of the sample.

The creep test used for the characterization of the polyurethane according to the present disclosure was performed in the following manner:

A polyurethane film with a thickness of 500±50 mm, cut into strips of 80 mm×15 mm, was used as sample. This copolymer film was obtained by drying, at a temperature of 22±2° C. and at a relative humidity of 50±5%, of solution or dispersion at 3% by weight of the polyurethane in water and/or ethanol.

Each strip was fixed between two jaws 50±1 mm apart, and was stretched at a speed of 20 mm/minute (under the above temperature and relative humidity conditions) to an elongation of 50% ($\epsilon_{max}$), i.e. up to 1.5 times its initial length. The stress was then released by imposing a return speed equal to the tension speed, i.e. 20 mm/minute, and the elongation of the sample (expressed as a % relative to the initial length) was measured immediately after returning to zero load ($\epsilon_i$).

The instantaneous recovery ($R_i$) was calculated using the following formula:

$$R_i(\%) = ((\epsilon_{max} - \epsilon_i)/\epsilon_{max}) \times 100$$

Quantification of the Hydrophobicity of the Polymer

The hydrophobicity of the polymer was measured on films via determination of the contact angles or drop angle.

When a drop of liquid is placed on a flat solid surface, the angle between the tangent to the drop at the point of contact and the solid surface is known as the contact angle (θ). It takes into account the amplitude of a liquid to spread out on a surface and depends on the interactions between the liquid and the solid.

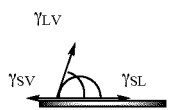

Measurement of this angle gives us several types of information:

if water is used as liquid for measuring the contact angle, the hydrophobic nature (low surface energy) or hydrophilic nature (high surface energy) of the surface may be deduced. Thus, the greater the contact angle, the more hydrophobic the surface;

measurement of the hysteresis between the angle at the leading edge of the drop and at the trailing edge of the drop gives information regarding the physical inhomogeneity (roughness) or chemical inhomogeneity of the surface.

Example 1

Step A

The following were introduced into a 1 liter reactor:

69.7 g of (12.9 mol %) of Polybd R45 HTLO from Sartomer, which is a polybutadiene resin containing hydroxyl end groups, 8.15 g (35.5 mol %) of N-methyldiethanolamine (NM-DEA), 0.025 g of dibutyltin dilaurate (DBTL) and 100 g of methyl ethyl ketone (MEK).

The medium was homogenized by stirring and with heating to 70° C. When the medium was homogeneous, 22.1 g (51.6 mol %) of isophorone diisocyanate (IPDI) were added and the mixture is refluxed for 8 hours.

After 8 hours, an infrared analysis of the reaction medium showed a weak residual NCO band at 2250 cm$^{-1}$. 10 g of ethanol and 130 g of methyl ethyl ketone were added, and the mixture was then allowed to return to room temperature.

A polymer solution with a final dry extract of 28% was obtained.

Step B 177 g of the above polymer solution at 28% in MEK were introduced into a 1 liter reactor and were then diluted with 105 g of THF (tetrahydrofuran). The solution was heated to 70° C. and 90 mol % of the amine functions were then neutralized by introducing 30.8 g of 1 N HCl. 250 g of water were then added and the organic solvents were distilled off under vacuum to obtain an opaque aqueous gel with a dry extract of 15.3%.

Example 2

Step A

The following were introduced into a 1 liter reactor:

70 g (11.4 mol %) of Krasol LBH-P 3000, which is a polybutadiene containing primary hydroxyl end groups, of Mn=3200, 8.8 g (38.6 mol %) of N-methyldiethanolamine (NM-DEA), 0.025 g of dibutyltin dilaurate (DBTL) and 100 g of methyl ethyl ketone (MEK).

The medium was homogenized with stirring and by heating to 70° C. When the medium was homogeneous, 21.2 g (49.9%) of isophorone diisocyanate were added and the mixture was refluxed for 8 hours.

After 8 hours, an infrared analysis of the reaction medium showed no more trace of residual NCO at 2250 cm$^{-1}$. 10 g of ethanol and 150 g of MEK were added and the mixture was then allowed to return to room temperature.

A polymer solution with a final dry extract of 28% was obtained.

Step B 180 g of the above polymer solution at 28% in MEK was introduced into a 1 liter reactor. The solution was heated to 70° C. and 90 mol % of the amine functions were then neutralized by introducing 33.2 g of 1N HCl. 87 g of water and 70 g of ethanol were then added to homogenize the medium. The dilution was completed with 370 g of water, and the mixture was then homogenized by adding 110 g of THF. The organic solvents were distilled off under vacuum to obtain an opaque aqueous gel with a dry extract of 10.9%.

The instantaneous recovery ($R_i$) was Ri=75.5%.

Example 3

Step A

The following were introduced into a 1 liter reactor:

70.9 g (7.9 mol %) of Krasol LBH 5000, which is a polybutadiene comprising secondary hydroxyl end groups, of Mn=3000, 9.1 g (42.3 mol %) of N-methyldiethanolamine (NM-DEA), 0.025 g of dibutyltin dilaurate (DBTL) and 100 g of methyl ethyl ketone (MEK).

The medium was homogenized with stirring and by heating to 70° C. When the medium was homogeneous, 20 g (49.8 mol %) of isophorone diisocyanate were introduced and the medium was refluxed for 8 hours.

After 8 hours, an infrared analysis of the reaction medium showed no more trace of residual NCO at 2250 cm$^{-1}$. 10 g of ethanol and 150 g of MEK were added and the mixture was then allowed to return to room temperature.

The polymer in solution, with a final dry extract of 28%, was obtained.

Step B 175 g of solution of the above polymer at 28% in MEK were introduced into a 1 liter reactor. The solution was diluted with 100 g of THF and then heated to 70° C. 90 mol % of the amine functions was neutralized by introducing 34.4 g of 1N HCl. 250 g of water and then 150 g of ethanol were then added to homogenize the medium. The organic solvents were then distilled off under vacuum to obtain an opaque white aqueous dispersion with a dry extract of 17.6% and a pH =4.1.

Example 4

Step A

The following were introduced into a 1 liter reactor:

70.5 g (4 mol %) of Krasol LBH 10 000, which is a polybutadiene comprising secondary hydroxyl end groups, of Mn=about 10 000, 9.8 g (46.2 mol %) of N-methyldiethanolamine (NM-DEA), 0.025 g of dibutyltin dilaurate (DBTL) and 100 g of methyl ethyl ketone (ME K).

The medium was homogenized with stirring and by heating to 70° C. When the medium was homogeneous, 19.7 g (49.8 mol %) of isophorone diisocyanate were introduced and the medium was refluxed for 8 hours.

After 8 hours, an infrared analysis of the reaction medium showed no more trace of residual NCO at 2250 cm$^{-1}$. 10 g of ethanol and 150 g of MEK were added and the mixture was then allowed to return to room temperature.

The polymer in solution, with a final dry extract of 29%, was obtained.

Step B 171 g of solution of the above polymer at 29% in MEK were introduced into a 1 liter reactor. 100 g of THF were added and the solution was heated to 70° C. 90 mol % of the amine fractions were neutralized by introducing 37 g of 1 N HCl. 250 g of water were then added. The organic solvents were distilled off under vacuum to obtain an opaque white aqueous dispersion with a dry extract of 17.6%.

Example 5

Step A

The following were introduced into a 1 liter reactor:
- 67.9 g (16 mol %) of Krasol LBH-P 2000, which is a polybutadiene comprising primary hydroxyl end groups, of Mn=2100,
- 8.7 g (34.4 mol %) of N-methyldiethanolamine (NMDEA),
- 0.025 g of dibutyltin dilaurate (DBTL) and
- 100 g of methyl ethyl ketone (MEK).

The medium was homogenized with stirring and by heating to 70° C. When the medium was homogeneous, 23.4 g (49.6 mol %) of isophorone diisocyanate were introduced and the medium was refluxed for 8 hours.

After 8 hours, an infrared analysis of the reaction medium showed the absence of NCO band at 2250 cm$^{-1}$. 10 g of ethanol and 150 g of THF were added and the reaction medium was then allowed to return to room temperature.

The polymer in solution, with a final dry extract of 25.5%, was obtained.

Step B 196 g of solution of the above polymer at 25.5% in the MEK/THF mixture, were introduced into a 1 liter reactor. The solution was heated to 70° C. and 90 mol % of the amine functions were then neutralized by introducing 32.9 g of 1N HCl. 300 g of water were then added and the reaction medium was then evaporated under vacuum to obtain an opalescent dispersion with a dry extract of 14.4% and of pH =4.5.

The instantaneous recovery ($R_i$) was Ri=72%. Mass: Mp=48 900 g/mol; Mn=31 100 g/mol; Mw=56 800 g/mol Ip=1.8

Step C 38 g of dry polymer, obtained by evaporation of the solvents and drying of the solution prepared in step A, were introduced into a 1 liter reactor and dissolved in 38 g of MEK by heating to 70° C. 40 mol % of the amine functions were neutralized by adding 11 g of 1 N HCl. 77 g of water were then added and the MEK was evaporated off under vacuum. A fluid opalescent latex (dispersion) was then obtained.

Example 6

The synthesis was identical to that of Example 5, except that 0.01% of catalyst was used instead of 0.025%.

Step A

The following were introduced into a 1 liter reactor:
- 203.7 g of Krasol LBH-P 2000,
- 26.1 g of N-methyldiethanolamine (NMDEA),
- 0.03 g of dibutyltin dilaurate (DBTL) and
- 300 g of methyl ethyl ketone (MEK).

The medium was homogenized with stirring and by heating to 70° C. When the medium was homogeneous, 70.2 g of isophorone diisocyanate were added and the mixture was refluxed for 8 hours.

After 8 hours, an infrared analysis of the reaction medium showed the absence of an NCO band at 2250 cm$^{-1}$. 30 g of ethanol were added and the reaction medium was then allowed to return to room temperature.

The polymer in solution, with a final dry extract of 53.5%, was obtained.

Mass: Mp=58 300 g/mol; Mn=37 500 g/mol; Mw=70 700 g/mol Ip=1.9

Step B 187 g of 53.5% solution of the polymer prepared in step A were introduced into a 1 liter reactor; 13 g of MEK were added to obtain a solution with a dry extract of 50%, and the solution was then heated to 70° C. 40 mol % of the amine functions were neutralized by adding 29.2 g of 1 N HCl. 204 g of water were then added and the MEK is evaporated off under vacuum. An opalescent dispersion with a dry extract of 30.1% was thus obtained.

The instantaneous recovery ($R_i$) was Ri=72%.

Step C 58.9 g of 53.5% solution of the polymer prepared in step A above were introduced into a 1 liter reactor; 8 g of MEK were added to obtain a solution with a dry extract of 50%. The solution was heated to 70° C. and 90 mol % of the amine functions were then neutralized by introducing 38.7 g of 1 N HCl. 295 g of water were then added and the MEK was then evaporated off under vacuum. A fluid opalescent latex with a dry extract of 14.8% was thus obtained.

The instantaneous recovery ($R_i$) was Ri=73%.

Step D 20 g of the polymer obtained in step A above was introduced into a 500 ml three-necked flask and diluted to 20% in MEK. 207.3 g of iodomethane (MeI) were added and the mixture was stirred at room temperature for 24 hours. After 24 hours, the medium had gelled and turned yellow.

200 g of the MEK/MeI mixture were distilled off by heating to 100° C. 200 g of MEK were then added and a further 200 g of solvent was distilled off to remove the traces of residual iodomethane.

162 g of water were then added with stirring and a two-phase medium was recovered, which evaporated under vacuum.

A white latex with a dry extract of 13.1% and of pH=5.5 was obtained.

The instantaneous recovery ($R_i$) was Ri=75%.

Mass: Mp=58 300 g/mol; Mn=37 500 g/mol; Mw=70 700 g/mol Ip=1.9

Comparative Example 7

A comparative polymer was prepared according to International Patent Application No. WO 02/32978.

Step A

The following were introduced into a 1 liter reactor:
- 70 g (12.5 mol %) of PTMO (polytetramethylene oxide) of Mn=2900,
- 8.6 g (37.5 mol %) of N-methyldiethanolamine (NMDEA),
- 0.025 g of dibutyltin dilaurate (DBTL) and
- 100 g of methyl ethyl ketone (MEK).

The medium was homogenized with stirring and by heating to 70° C. When the medium was homogeneous, 21.4 g (50 mol %) of isophorone diisocyanate were added and the mixture was refluxed for 8 hours.

After 8 hours, an infrared analysis of the reaction medium showed the absence of an NCO band at 2250 cm$^{-1}$. 10 g of ethanol were added and the reaction medium was then allowed to return to room temperature.

The polymer in solution, with a final dry extract of 50%, was obtained.

Step B 200 g of solution of the above polymer with a dry extract of 50% were introduced into a 1 liter reactor. The solution was heated to 70° C. and 90 mol % of the amine functions was then neutralized by introducing 64.9 g of 1 N HCl. 400 g of water were then added and the reaction medium was then evaporated under vacuum to obtain an opalescent dispersion with a dry extract of 20%.

Step C

The following three polymers were compared:

|  | Prepolymer | NMDEA | IPDI | Neutralization |
|---|---|---|---|---|
| Comparative polymer 7B | PTMO 2900 70% | 8.6% | 21.4% | 90% of the amine units |
| Polymer invention 5B | Krasol LBH P2000 67.9% | 8.7% | 23.4% | 90% of the amine units |
| Polymer invention 5C | Krasol LBH P2000 67.9% | 8.7% | 23.4% | 40% of the amine units |

Preparation of the Films:

The polymer dispersions of Examples 5B, 5C and 7B were diluted to 13% with HPLC water. 2 ml of dispersion were then placed on 1 cm×5 cm glass plates. The films were left to dry at ambient temperature and humidity (20° C.) for 24 hours.

Measurement of the contact angles:
Machine brand: GBX
Machine name: DGD Fast 160 Contact Angle Meter
Parameters: Method: Manual 2; photos at 100 ms; drop volume 3.5 μl; vertical displacement: 95
Liquid used: water The measurements were performed on the left and right angles of the drop; several measurements were taken so as to obtain a mean value.

The contact angle values measured are given in the table below.

|  |  | Left angle in ° | Right angle in ° | Mean θ |
|---|---|---|---|---|
| Comparative Example 7B | Measurement 1 | 81.9 | 81.9 | 79.6 |
|  | Measurement 2 | 76.6 | 76.6 |  |
|  | Measurement 3 | 80.4 | 79.9 |  |
| Example 5B | Measurement 1 | 92.8 | 92.8 | 90.1 |
|  | Measurement 2 | 87.0 | 87.0 |  |
|  | Measurement 3 | 90.5 | 90.5 |  |
| Example 5C | Measurement 1 | 100.6 | 100 | 99.8 |
|  | Measurement 2 | 97.7 | 99.1 |  |

The comparative polymer was markedly more hydrophilic than the polymers according to the present disclosure. The incorporation of a polybutadiene segment thus made it possible to render the material more hydrophobic and more water resistant.

Moreover, it was found that the deposit placed on a lock of hair ("strand") onto which the comparative polymer 7B had been applied (as a lotion, impregnation, drying under a hood) was less water resistant than that obtained with polymers 5B or 5C.

The comparative polymer 7B formed a tacky strand, whereas polymers 5B and 5C according to the present disclosure gave non-tacky strands.

Example 8

A hair composition of lacquer type was prepared, comprising:

| polymer of Example 1 | 6% AM (active material |
|---|---|
| demineralized water | qs 100% |
| dimethyl ether: 35 g of gas per 65 g of 6% polymer dispersion | |

Example 9

A hair composition of styling mousse type was prepared, comprising:

| polymer of Example 1 | 6% AM (active material) |
|---|---|
| demineralized water | qs 100% |
| isobutane/propane/butane mixture: 5 g of gas per 95 g of the 6% polymer dispersion. | |

What is claimed is:

1. A polyurethane comprising:
(a1) at least one cationic or cationizable unit derived from at least one tertiary or quaternary amine comprising at least two reactive functions containing labile hydrogen, wherein the amines forming the units (a1) are chosen from compounds of formulae:

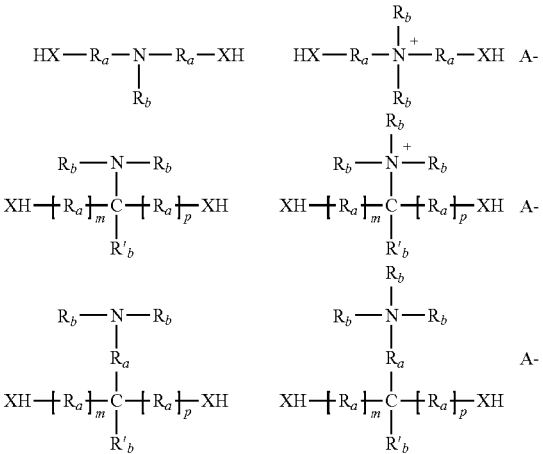

wherein:
each $R_a$, independently of each other, is a linear or branched divalent $C_1$-$C_6$ alkylene group, or alternatively a $C_3$-$C_6$ cycloalkylene or arylene group, or mixtures thereof; these groups optionally being substituted with at least one halogen atom and/or optionally comprising at least one heteroatom chosen from O, N, P and S,
each $R_b$ is, independently of each other, a linear or branched $C_1$-$C_6$ alkyl group or alternatively a $C_3$-$C_6$ cycloalky or arly group, or mixtures thereof; these groups optionally being substituted with at least one halogen atom and/or optionally comprising at least one heteroatom chosen from O, N, P and S,
each R'b is chosen from H and a linear or branched $C_1$$C_6$ alky group, or alternatively a $C_3$-$C_6$ cycloalkyl or aryl group, or mixtures thereof; these groups optionally being substituted with at least one halogen atom and/or optionally comprising at least one heteroatom chosen from O, N, P and S,
m and p are, independently of each other, equal to 0 or 1;
each X is, independently, an oxygen or sulfur atom, or a group NH or $NR_c$, wherein $R_c$ is a $C_1$-$C_6$ alkyl group, and $A^-$ is a physiologically acceptable counterion;
(a2) at least one nonionic unit derived from at least one polyolefin comprising at least two reactive functions containing labile hydrogen said polyolefin comprising at least 10 mol % of units comprising at least one C=C double bond, relative to the total amount of units forming said polyolefin;
wherein the at least one polyolefin has hydroxyl end groups and is chosen from:
at least one olefin homopolymer chosen from 1,2-butadiene, 1,4-butadiene and isoprene homopolymers in their cis and trans forms; 1,2-polybutadienes, poly(cis-1,4-isoprenes) and poly(trans-1,4-isoprenes); or
at least one statistical olefin copolymer corresponding to the following structure:

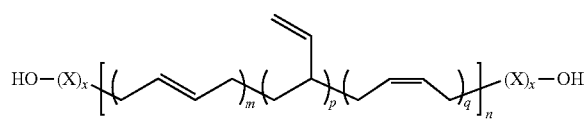

wherein:
m, p and q are mole fractions ranging from 0 to 1, and m+p+q=1;
n is an integer ranging from 10 to 100;
x is 0 or 1, and
X is a divalent carbon-based radical comprising 1 to 10 carbon atoms; and
(b) at least one unit derived from a compound comprising at least two isocyanate functions.

2. A polyurethane according to claim 1, wherein said counterion $A^-$ is a halide.

3. A polyurethane according to claim 1, wherein the amines are:
of formula:

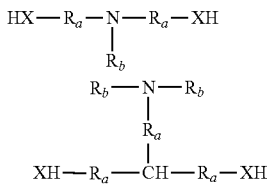 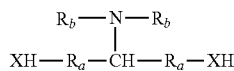

in which formulas above or in the amine formulas in claim 1
Ra is a linear or branched divalent $C_1$-$C_6$ alkylene group; and/or
Rb is a linear or branched $C_1$-$C_6$ alkyl group; and/or
X=O.

4. A polyurethane according to claim 3, wherein the amines are of formula:

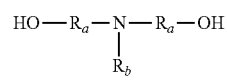

wherein Ra is a linear or branched divalent $C_1$-$C_6$ alkylene group; and Rb is a linear or branched $C_1$-$C_6$ alkyl group.

5. A polyurethane according to claim 1, wherein the amines are chosen from N-methyldiethanolamine and N-tert-butyldiethanolamine.

6. A polyurethane according to claim 1, wherein m ranges from 0.15 to 0.7, p ranges from 0.15 to 0.7, q ranges from 0.1 to 0.4, and n is an integer ranging from 15 to 50.

7. A polyurethane according to claim 1, wherein the at least one polyolefin is chosen from:
polybutadienes with hydroxyl end groups;
polybutadienes with primary hydroxyl end groups; and
polybutadienes with secondary hydroxyl end groups.

8. A polyurethan according to claim 7, wherein the at least one polyolefin is chosen from:
polybutadienes with hydroxyl end groups corresponding to the following structure:

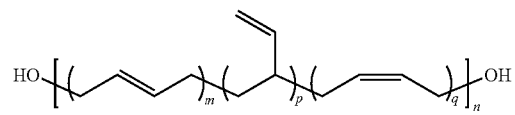

wherein m=0.6, p=q=0.2 and n=25;
polybutadienes with primary hydroxyl end groups, of structure:

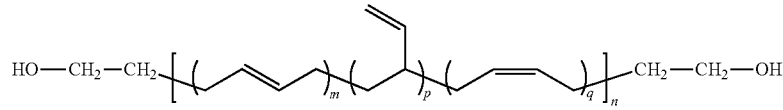

with m=0.17, p=0.65 and q=0.18, and n is such that the number-average molecular weight Mn ranges from 1000 to 10,000; and
polybutadienes with secondary hydroxyl end groups corresponding to the following structure:

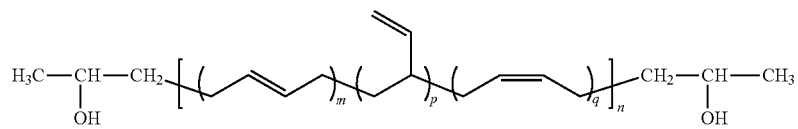

with m=0.17, p=0.65 and q=0.18 and n is such that the number-average molecular weight Mn ranges from 1000 to 12000.

9. A polyurethane according to claim 1, wherein the polyolefin comprising at least two reactive functions containing labile hydrogen, forming the nonionic units (a2), is a copolymer also comprising additional units not comprising a C=C double bond, present in a maximum amount of 90 mol %.

10. A polyurethane according to claim 9, wherein the additional units are chosen from ethylene —$(CH_2—CH_2)_n$—, propylene —$(CH_2—CH_2—C_2)_n$— or isopropylene —$(CH_2CH(CH_3))_n$—, units, and/or butylene units of formula:

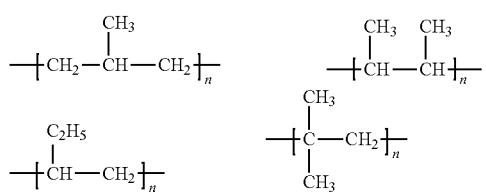

and also mixtures thereof.

11. A polyurethane according to claim 1, wherein the at least one polyolefin that may be used to form the units (a2) comprises at least 20 mol % of units comprising at least one C=C double bond, relative to the total amount of units forming said polyolefin.

12. A polyurethane according to claim 11, wherein the at least one polyolefin that may be used to form the units (a2) comprises 100 mol % of units comprising at least one C=C double bond, relative to the total amount of units forming said polyolefin.

13. A polyurethane according to claim 1, wherein the at least one polyolefin is chosen from:
  1,4-polybutadiene and 1,2-polybutadiene homopolymers having hydroxyl end groups; and
  copolymers of structure:

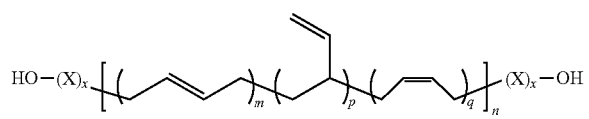

wherein
  m, p and q are mole fractions ranging from 0 to 1, and m+p+q=1;
  p ranges from 0.1 to 0.8; and q ranges from 0.05 to 0.5;
  n is an integer ranging from 10 to 100;
  x is 0 or 1, and
  X is a divalent carbon-based radical comprising 1 to 10 carbon atoms.

14. A polyurethane according to claim 13, wherein the at least one polyolefin is chosen from 1,4-polybutadiene and 1,2-polybutadiene homopolymers haying hydroxyl end groups.

15. A polyurethane according to claim 13 wherein in said copolymers, m ranges from 0.15 to 0.7, p ranges from 0.15 to 0.7, q ranges from 0.1 to 0.4, and n is an integer ranging from 15 to 50.

16. A polyurethane according to claim 1, wherein the at least one polyolefin forming the nonionic units (a2) has a number-average molecular mass (Mn) ranging from 400 to 50000.

17. A polyurethane according to claim 16, wherein the at least one polyolefin forming the nonionic units (a2) has a number-average molecular mass (Mn) ranging from 1500 to 12000.

18. A polyurethane according to claim 1, wherein the compound comprising at least two isocyanate functions is choesn from diisocyanates, or mixtures of a diisocyanate and of a polyisocyanate comprising more than two isocyanate functions, wherein said polyisocyanate representes 0.1% to 40% of the weight of the mixture.

19. A polyurethane according to claim 18, wherein said polyisocyanate representes 0.1% o 30% of the weight of the mixture.

20. A polyurethane according to claim 1, wherein the compound comprising at least two isocyanate functions is chosen from conjugated or non-conjugated, aromatic or non-aromatic cyclic aliphatic diisocyanates.

21. A polyurethane according to claim 1, in which the compound comprising at least two isocyanate functions is chosen from methylenediphenyl diisocyanate, methylenecyclohexane diisocyanate, isophorone diisocyanate, toluene diisocyanate, naphthalene diisocyanate, 1,4-butane diisocyanate and 1,6-hexane diisocyanate, and mixtures thereof.

22. A polyurethane according to claim 1, comprising:
  at least one cationic unit resulting from amines of formula:

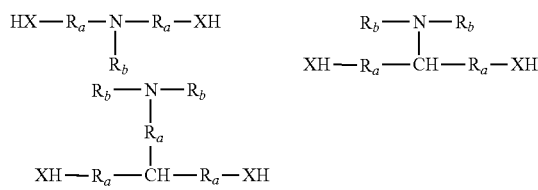

wherein:
  Ra is a linear or branched divalent $C_1$-$C_6$ alkylene group;
  Rb is a linear or branched $C_1$-$C_6$ alkyl group;
  and X is O;
  at least one nonionic unit resulting from polyolefins chosen from 1,4-polybutadiene and 1,2-polybutadiene homopolymers; or copolymers of structure:

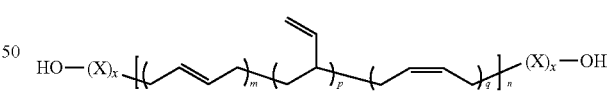

wherein
  m, p and q are mole fractions ranging from 0 to 1, and m+p+q=1;
  p ranges from 0.1 to 0.8; q ranges from 0.05 to 0.5;
  n is an integer ranging from 10 to 100;
  x=0 or 1, and
  X is equal to a divalent carbon-based radical comrising 1 to 10 carbon atoms; and
  at least one unit resulting from aliphatic diisocyanates.

23. A polyurethane according to claim 22, wherein m ranges from 0.15 to 0.7, p ranges from 0.15 to 0.7, q ranges from 0.1 to 0.4, and n is an integer ranging from 15 to 50.

24. A polyurethane according to claim 1, comprising:
at least one cationic unit resulting from amines of formula:

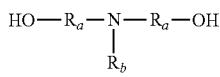

wherein Ra is a linear or branched divalent $C_1$-$C_6$ alkylene group; and Rb is a linear or branched $C_1$-$C_6$ alkyl group;
at least one nonionic unit resulting from polyolefins of structure:

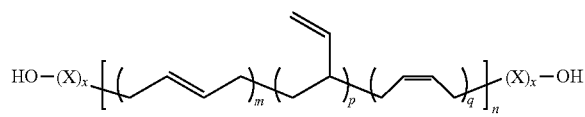

wherein
m, p and q are mole fractions ranging from 0 to 1, and m+p+q=1;
p ranges from 0.1 to 0.8; and q ranges from 0.05 to 0.5;
n is an integer ranging from 10 to 100;
x=0 or 1, and
X is a divalent carbon-based radical, comprising 1 to 10 carbon atoms; and
at least one unit resulting from diisocyanates chosen from methylenecyclohexane diisocyanate, isophorone diisocyanate, 1,4-butane diisocyanate and 1,6-hexane diisocyanate, and mixtures thereof.

25. A polyurethane according to claim 24, wherein m ranges from 0.15 to 0.7, p ranges from 0.15 to 0.7, q ranges from 0.1 to 0.4, and n is an integer ranging from 15 to 50.

26. A polyurethane according to claim 1 wherein:
the amines forming the cationic or cationizable units (a1) represent from 0.1% to 50% by weight, relative to the total weight of the final polyurethane; and/or
the polyolefins forming the nonionic units (a2) represent from 30% to 99% by weight, relative to the total weight of the final polyurethane; and/or
the compounds comprising at least two isocyanate functions forming the units (b) represent from 1% to 60% by weight, relative to thte total weight of the final polyurethane.

27. A polyurethane according to claim 26, wherein the amines forming the cationic or cationizable units (a1) represent from 5% to 20% by weight relative to the total weight of the final polyurethane.

28. A polyurethane according to claim 26, wherein the polyolefins forming the nonionic units (a2) represent from 60% to 80% by weight relative to the total weight of the final polyurethane.

29. A polyurethane according to claim 26, wherein the polyolefins forming the compounds comprising at least two isocyanate functions forming the units (b) represent from 15% to 35% by weight relative to the total weight of the final polyurethane.

30. A cosmetic or pharmaceutical composition comprising, in a physiologically acceptable medium, at least one polyurethane comprising:
(a1) at least one cationic or cationizable unit derived from at least one tertiary or quaternary amine comprising at least two reactive functions containing labile hydrogen,
(a2) at least one nonionic unit derived from at least one polyolefin comprising at least two reactive functions containing labile hydrogen, said polyolefin comprising at least 10 mol % of units comprising at least one C=C double bond, relative to the total amount of units forming said polyolefin;
wherein the at least one polyolefin has hydroxyl end groups and is chosen from:
at least one olefin homopolymer chosen from 1,2-butadiene, 1,4-butadiene and isoprene homopolymers in their cis and trans forms; 1,2-polybutadienes, poly(cis-1,4-isoprenes) and poly(trans-1,4-isoprenes); or
at least one statistical olefin copolymer corresponding to the following structure:

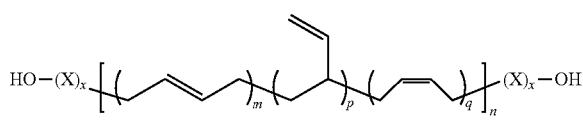

wherein:
m, p and q are mole fractions ranging from 0 to 1, and m+p+q=1;
n is an integer ranging from 10 to 100;
x is 0 or 1, and
X is a divalent carbon-based radical comprising 1 to 10 carbon atoms; and
(b) at least one unit derived from a compound comprising at least two isocyanate functions.

31. A composition according to claim 30, wherein the polyurethane is present in an amount ranging from 0.1% to 90% by weight relative to the weight of the composition.

32. A composition according to claim 31, wherein the polyurethane is present in an amount ranging from 6% to 10% by weight relative tot the weight of the composition.

33. A composition according to claim 30, wherein the physiologically acceptable medium comprises at least one compound chosen from water, alcohols, polyols, polyol or glycol ethers, hydrophilic $C_2$-$C_4$ aldehydes, esters, carbon-based oils, silicone oils, fluorosilicone oils; gelling agents and/or thickeners such as anionic, nonionic or cationic associative or non-associative polymers; anionic, nonionic, cationic and/or amphoteric surfactants; pro-penetrating agents, emulsifiersl, fragrances, preserving agents, fillers, sunscreens; silicones; dyestuffs, proteins, vitamins, provitamins; fixing or non-fixing, anionic, nonionic, cationic or amphoteric polymers; moisturizers, emollients, softeners; mineral, plant or synthetic oils; hydrophilic or lipophilic active agents; antifoams, antiperspirants, free-radical scavengers, bactericidal agents and anti-dandruff agents; and also mixtures thereof.

34. A composition according to claim 30, which is in a form chosen from a product for caring for, cleaning and/or making up bodily or facial skin, the lips, the eyelashes, the nails and the hair; an antisun or self-tanning product; a body hygiene product; and a hair product.

35. A composition according to claim 30, which is in the form of a hair composition for holding the hairstyle or for shaping the hair.

36. A composition according to claim 30, which is in the form of a hair composition of hair lacquer type, and in which the polyurethane is present in an amount ranging from 0.1% to 25% by weight, relative to the weight of the composition.

37. A composition according to claim 36, wherein the polyurethane is present in an amount ranging from 4% to 8% by weight relative tot the weight of the composition.

38. A composition according to claim 30, which is in the form of a styling composition in which the polyurethane is present in an amount ranging from 0.5% to 20% by weight, relative to the weight of the composition.

39. A composition according to claim 38, wherein the polyurethane is present in an amount ranging from 5% to 8% relative to the weight of the composition.

40. A composition accordin gto claim 30, which is in the form of a hair composition of shampoo type in which the polyurethane is present in an amount ranging from 0.1% to 20% by weight, relative to the weight of the composition.

41. A composition according to claim 40, wherein the polyurethane is present in an amount ranging from 2% to 5% relative to the weight of the composition.

42. A cosmetic treatment process for making up, caring for, cleansing, coloring or shaping keratin materials comprising applying to said keratin materials a cosmetic composition comprising, in a physiologically acceptable medium, at least one polyurethane comprising:
A cosmetic or pharmaceutical composition comprising, in a physiologically acceptable medium, at least one polyurethane comprising
  (a1) at least one cationic or cationizable unit derived from at least one tertiary or quaternary amine comprising at least two reactive functions containing labile hydrogen,
  (a2) at least one nonionic unit derived from at least one polyolefin comprising at least two reactive functions containing labile hydrogen, said polyolefin comprising at least 10 mol % of units comprising at least one C=C double bond, relative to the total amount of units forming said polyolefin;
wherein the at least one polyolefin has hydroxyl end groups and is chosen from:
at least one olefin homopolymer chosen from 1,2-butadiene, 1,4-butadiene and isoprene homopolymers in their cis and trans forms; 1,2-polybutadienes, poly(cis-1,4-isoprenes) and poly(trans-1,4-isoprenes); or
at least one statistical olefin copolymer corresponding to the following structure:

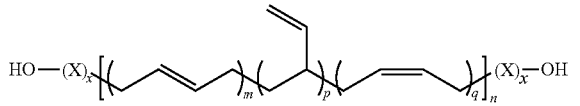

wherein:
m, p and q are mole fractions ranging from 0 to 1, and m+p+q=1;
n is an integer ranging from 10 to 100;
x is 0 or 1, and
X is a divalent carbon-based radical comprising 1 to 10 carbon atoms; and
  (b) at least one unit derived from a compound comprising at least two isocyanate functions.

43. A cosmetic treatment process for shaping and/or holding the hair, comprising applying to hair a cosmetic composition comprising, in a physiologically acceptable medium, at least one polyurethane comprising:
  (a1) at least one cationic or cationizable unit derived from at least one tertiary or quaternary amine comprising at least two reactive functions containing labile hydrogen,
  (a2) at least one nonionic unit derived from at least one polyolefin comprising at least two reactive functions containing labile hydrogen, said polyolefin comprising at least 10 mol % of units comprising at least one C=C double bond, relative to the total amount of units forming said polyolefin;
wherein the at least one polyolefin has hydroxyl end groups and is chosen from:
at least one olefin homopolymer chosen from 1,2-butadiene, 1,4-butadiene and isoprene homopolymers in their cis and trans forms; 1,2-polybutadienes, poly(cis-1,4-isoprenes) and poly(trans-1,4-isoprenes); or
at least one statistical olefin copolymer corresponding to the following structure:

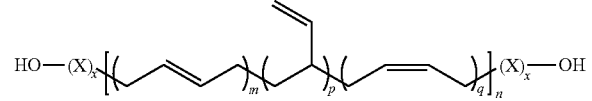

wherein:
m, p and q are mole fractions ranging from 0 to 1, and m+p+q=1;
n is an integer ranging from 10 to 100;
x is 0 or 1, and
X is a divalent carbon-based radical comprising 1 to 10 carbon atoms; and
  (b) at least one unit derived from a compound comprising at least two isocyanate functions;
optionally followed by a rinsing step.

* * * * *

UNITED STATES PATENT AND TRADEMARK OFFICE
CERTIFICATE OF CORRECTION

PATENT NO. : 8,449,871 B2
APPLICATION NO. : 11/723455
DATED : May 28, 2013
INVENTOR(S) : Nathalie Mougin et al.

It is certified that error appears in the above-identified patent and that said Letters Patent is hereby corrected as shown below:

In the Claims

Col. 20, Claim 1, line 55, "C1C6" should be -- C1-C6 --.

Signed and Sealed this
Sixth Day of August, 2013

Teresa Stanek Rea
*Acting Director of the United States Patent and Trademark Office*